(12) United States Patent
Tottewitz et al.

(10) Patent No.: US 7,594,449 B2
(45) Date of Patent: Sep. 29, 2009

(54) HOLDER ARMATURE FOR AN INTERCHANGEABLE MEASURING PROBE

(75) Inventors: Michael Tottewitz, Karlsdorf-Neuthard (DE); Daniel Caderas, Lohn (CH)

(73) Assignee: Mettler-Toledo AG, Greifensee (CH)

( * ) Notice: Subject to any disclaimer, the term of this patent is extended or adjusted under 35 U.S.C. 154(b) by 479 days.

(21) Appl. No.: 11/463,319

(22) Filed: Aug. 9, 2006

(65) Prior Publication Data

US 2007/0034028 A1 Feb. 15, 2007

(30) Foreign Application Priority Data

Aug. 10, 2005 (EP) ................... 05107332

(51) Int. Cl.
*G01D 21/00* (2006.01)
(52) U.S. Cl. .................................... 73/866.5
(58) Field of Classification Search ................ 73/865.5, 73/86, 863.82, 863.86, 756, 1.06, 1.07, 1.02, 73/866.5; 375/208
See application file for complete search history.

(56) References Cited

U.S. PATENT DOCUMENTS

| | | | |
|---|---|---|---|
| 5,639,975 A * | 6/1997 | Waterman | 73/866.5 |
| 5,939,610 A | 8/1999 | Iwamoto | |
| 5,962,795 A * | 10/1999 | Lambert | 73/866.5 |
| 6,131,473 A | 10/2000 | Hoffman | |
| 6,640,658 B1 * | 11/2003 | Guerrero et al. | 73/866.5 |
| 6,772,652 B2 * | 8/2004 | Cronimus | 73/866.5 |
| 7,121,158 B2 * | 10/2006 | Scott et al. | 73/866.5 |
| 2005/0229727 A1 | 10/2005 | Caderas | |

FOREIGN PATENT DOCUMENTS

DE   G9211897.6 U1   12/1992
EP   0882896 B1    1/1998

* cited by examiner

*Primary Examiner*—Robert R Raevis
(74) *Attorney, Agent, or Firm*—Standley Law Group LLP

(57) ABSTRACT

An armature for holding an interchangeable measuring probe, has a housing (2), an immersion tube (3) that removably receives the probe and which is axially movable in the housing between a rest position and a measuring position, a drive mechanism arranged in a drive mechanism housing (17, 26), and a drive element (4) designed to be coupled to the immersion tube. The immersion tube and/or the measuring probe are always located outside of the drive mechanism housing. A housing attachment (25) is arranged between the housing and the drive mechanism housing, the housing attachment being connected to the housing in a releasable manner.

23 Claims, 3 Drawing Sheets

HOLDER ARMATURE FOR AN INTERCHANGEABLE MEASURING PROBE

CROSS-REFERENCE TO RELATED APPLICATIONS

The present application claims a right of priority under 35 USC §119 from European patent application 05 107 332.8, filed 10 Aug. 2005, the content of which is incorporated by reference as if fully recited herein.

TECHNICAL FIELD

The invention relates to a probe-holder armature for an interchangeable measuring probe.

BACKGROUND OF THE ART

Probe-holder armatures are a means whereby a measuring probe that is in most cases of a standardized design can be installed and/or uninstalled in a simple manner for example in a chemical, pharmaceutical or biological process or in a container in which such a process takes place. It can become necessary to remove a measuring probe from a process for example in order to exchange a defective measuring probe, or in order to protect the measuring probe for example when the process system is being cleaned. The known types of holder armatures for interchangeable probes are therefore in many cases equipped with a treatment chamber in which the measuring probe can be, among other things, cleaned, subjected to a function test, and/or calibrated in separation from the process apparatus. Holder armatures for interchangeable probes are used for example together with different measuring probes, such as pH probes, conductivity probes, ion-sensitive probes, turbidity-measuring probes, or gas probes, among others.

Holder armatures for interchangeable probes of the known types are designed in a substantially cylindrical shape. A measuring probe is inserted into the holder armature from the end that faces away from the measurement medium, so that a cable that is connected to the measuring probe will exit at that end from the armature. In the exchange of the measuring probe, it can happen that the latter is simply pulled out of the holder armature by the probe cable, whereby the cable can in some cases be forcibly separated from the measuring probe. In addition, the cable can also be stressed by a pulling force during operation of the armature, whereby the connection between the cable and the measuring probe can be weakened.

In view of the conditions that holder armatures for interchangeable probes are exposed to in chemical processes, the design of the armatures has to be very much safety-oriented, so as to prevent the possibility that the measuring probe is inadvertently removed from the holder armature.

The applicant's European patent application EP 0 882 896 A1 discloses a holder armature for interchangeable probes in which a measuring probe is arranged in an immersion tube in a way that allows the probe to be taken out of the tube. The immersion tube is arranged in a housing in which the tube is axially movable between a rest position and a measuring position. Between the immersion tube and the measuring probe that is arranged inside it, there is at least one seal which seals the immersion tube against the measurement medium. This holder armature comprises a locking element which prevents axial movement of the immersion tube when no measuring probe is in place.

A holder armature for interchangeable probes which has a treatment chamber and a locking element against inadvertent removal of the measuring probe is disclosed in applicant's U.S. patent application, which is co-pending as U.S. Ser. No. 11/075,483 and which has been published as US 2005/0229727 A1. This holder armature is likewise designed so that the measuring probe is inserted from the end of the holder armature that is farther from the measurement medium into the immersion tube that is located inside the holder armature. As a locking element, the immersion tube has an insert which can be fixedly secured, whereby the measuring probe is pushed against a stop which is located inside the immersion tube and directed towards the measurement medium.

In spite of the safety measures that are known at this state of the art, it would certainly still be possible in principle to pull the measuring probe from the holder armature with brute force, even if the immersion tube is in the measuring position. This would have the consequence that the measurement medium could enter into the holder armature and also escape from there into the environment, a risk which especially with aggressive and/or toxic media must be avoided under all circumstances.

State-of-the-art holder armatures for interchangeable measuring probes have an immersion tube which is axially movable in a housing and in which the measuring probe can be arranged. This immersion tube is matched at least to the length of the measuring probe. The length of the immersion tube often determines the maximum outside height of the holder armature, i.e. the height of the part of the armature that is on the outside of the container. Especially when long sensor probes are used, the immersion tube can protrude in its rest position from the holder armature or from the housing of the latter at the end that points away from the measurement medium. When changing from the rest position into a measuring position, the immersion tube together with the measuring probe arranged inside it is moved axially in the housing in the direction towards the measurement medium. The installation height of the state-of-the-art holder armatures for interchangeable probes therefore varies depending on where the immersion tube is positioned within its displacement range and depending on the measuring probe that can be arranged in the immersion tube. The installation height needs to be considered especially in the design of process systems in order to provide enough clear space to allow the removal of the measuring probe from the holder armature. The holder armature should preferably be integrated in the system in such a way that the armature is easily accessible, but that the change of the outside height when the immersion tube is moved to a different position does not pose a danger to parts of the process system, to nearby objects, or even to persons that may be present in the vicinity.

The invention therefore has the objective to propose an improved design for a holder armature for interchangeable measuring probes, which is in particular safe to operate, and which overcomes the drawbacks described above.

SUMMARY OF THE INVENTION

The solution to meet this objective is offered by a holder armature for an interchangeable measuring probe in accordance with the appended claims.

A holder armature for an interchangeable measuring probe comprises a housing, an immersion tube that is axially movable in said housing between a rest position and a measuring position, a measuring probe which can be arranged in the immersion tube in a way that allows the probe to be taken out of the tube, a drive mechanism arranged in a drive mechanism housing, and a drive element that can be coupled to the immersion tube, wherein the immersion tube and a measuring probe that can be placed in the immersion tube are always outside of the drive mechanism housing.

Arranged between the housing and the drive mechanism housing occupied by the drive mechanism is a housing attachment which is releasably connected to the housing and accommodates the drive element. The housing attachment provides a spatial separation of the drive mechanism from the housing and allows in combination with the drive element a thermal disconnection between the drive mechanism and the housing. This is particularly advantageous, since heat that is generated in the drive mechanism housing can have no influence on the housing nor on the immersion tube arranged in the housing, nor on the measuring probe that can be arranged in the immersion tube.

The releasable connection between the drive mechanism and the immersion tube is particularly advantageous, because this allows the use of a drive mechanism that is arranged in a drive mechanism housing and is almost completely encapsulated. This arrangement leaves no passage opening in the drive mechanism nor in the drive mechanism housing for the immersion tube and/or the measuring probe that can be arranged in the immersion tube. The drive mechanism and the drive element can be separated from the holder armature, so that the exchange of a measuring probe that may be installed in the immersion tube can be performed in a simple and safe manner without having to move the measuring probe through the drive mechanism. The measuring probe is designed to be inserted in the holder armature, which means that a measuring probe can be removed from as well as set into the holder armature, or that it can also be exchanged for another measuring probe.

The housing attachment has a releasable connection to the housing and preferably a fixed connection to the drive mechanism housing. To perform an exchange of the measuring probe that is removable from the immersion tube, the drive mechanism housing together with the drive element and the housing attachment can be removed completely from the housing, or it can also be merely moved relative to the housing and/or opened, so that an opening of the immersion tube is directly accessible and a measuring probe can easily be inserted in or removed from the immersion tube.

The arrangement of the housing attachment between the drive mechanism housing and the housing is particularly advantageous because a holder armature that is configured in this manner has a fixed outside height. A change in the position of the immersion tube by sliding the latter in or out will not change the outside height of the holder armature.

It is advantageous to configure the holder armature in such a way that the drive mechanism housing is free of passage openings for conduits to and/or from the measuring probe. All conduit lines to and/or from the measuring probe can be arranged to pass through the side of the holder armature, so that only the drive element is connected directly to the drive mechanism. The term "conduit lines" in this context means primarily cables serving to transmit either power and/or data to and from the measuring probe and to perform the transmission to an appropriate processing- and/or control unit or an operation control center.

In a preferred embodiment, a treatment chamber is arranged in the housing for the measuring probe which can be inserted in the immersion tube. The treatment chamber is designed in such a way that a measuring probe which is set in place in the immersion tube can—in the rest position—be cleaned, calibrated and/or function-tested, depending on the type of the measuring probe being used.

The treatment chamber therefore has at least one conduit terminal through which a variety of known cleaning and calibrating solutions as well as gases can be carried in and out or a vacuum can be drawn. Especially when using liquids or gases as treatment agents, it suggests itself that the treatment chamber be equipped with more than one conduit terminal. The treatment agents can be removed again from the treatment chamber either by the same or at least one additional conduit terminal.

The drive element is preferably configured in the form of a rod or a sleeve, as well as with axial mobility, and is connected to the drive mechanism. At the end that is nearer to the measurement medium, the drive element has an opening which can receive the sensor head, i.e., the part of the measuring probe that is at the opposite end from the measurement medium, or which can also serve as cable guide for a cable that is attached to the sensor head. The configuration as a cable guide is relevant only for measuring probes in which the exchange of power and/or data runs through a cable, i.e. in cases where the connection is not wireless. Due to the design of the drive element, the cable exits through the side of the holder armature and is therefore always relieved of tension. To install and uninstall the measuring probe, the latter can be held by the sensor head without exerting a pull on the cable.

The drive element can be coupled to the immersion tube and can be moved together with the latter from the rest position to the measuring position by means of the drive mechanism. The drive element is configured so that it can receive the sensor head. In the rest position, the drive element is located in the housing attachment and in the drive mechanism housing; in the measuring position, the drive element is moved towards the measurement medium and is in this case located substantially in the housing attachment and in the adjoining housing.

The drive element and the housing attachment in which it is located are designed in such a way that the measuring probe can be removed or inserted in the holder armature only in the rest position with the housing attachment opened or released and with the immersion tube and the drive element disconnected from each other. The housing attachment together with the drive mechanism housing and the drive element can be completely removed from the housing. However, an arrangement is preferred where the housing attachment has a swivel connection to the housing through a non-centrically arranged axle.

It is advantageous if the housing attachment is connected to the housing at only one hinge location and is of a design which is as much as possible closed off from the outside, preferably with at least one cable-guide passage in the housing attachment for a cable that may be connected with the measuring probe. Thus, the measuring probe cannot be removed from the holder armature if the housing attachment and the housing are closed. A housing attachment that is closed off as much as possible has the further advantage that liquids and/or dust particles can be prevented from penetrating into the holder armature from the outside.

An inadvertent removal of the measuring probe from the immersion tube is prevented already by the design of the drive element and the housing attachment. Additionally, the holder armature can be equipped with at least one safety element. The at least one safety element prevents an axial displacement of the immersion tube when there is no measuring probe in the immersion tube and/or when the housing attachment is opened and/or when there is no correct connection between the immersion tube and the drive element. One or more safety elements can be arranged at different positions in the holder armature.

A safety element can also serve for the purpose of controlling the opening of the at least one inlet conduit to the treatment chamber, so that the treatment chamber can only be used if a measuring probe is located in the immersion tube and the latter is in the rest position.

The at least one safety element can be configured as a mechanical and/or electronic locking element. A mechanical locking element can be for example a bolt which engages a recess in the immersion tube and thus prevents an axial displacement of the immersion tube. However, a locking element can also be designed as an electrical device, so that the drive mechanism is immobilized for example in the absence of electrical contact between two elements.

Process systems are generally controlled and monitored by a process-monitoring and/or control center. A process system can have one or more holder armatures for interchangeable probes. It suggests itself in this case to design the at least one safety element as an electronic sensor which can, like the electronic locking element, control the drive mechanism and/or send a signal to the control center, so that a report arrives there regarding the condition of a specific holder armature. This is particularly advantageous and user friendly, as several holder armatures can be monitored simultaneously from a central place and defective armatures can for example be specifically identified.

In order to prevent that any of the measurement medium can get inside the holder armature, the immersion tube and/or the housing has at least one seal which seals the treatment chamber in the measuring position against the measurement medium and/or in the rest position against the measurement medium as well as against the ambient environment.

A preferred embodiment has at least one further seal which is arranged at the immersion tube and/or at the housing and which ensures in the rest position that the treatment chamber is sealed against the measurement medium as well as against the drive element and the housing attachment in which the drive element is located.

The drive mechanism as well as the drive mechanism housing of the holder armature can be designed either in a straight line-up or in an angled configuration. Using a drive mechanism arranged at an angle suggests itself for example in some locations in an industrial system with tight spatial conditions.

The drive mechanism for a holder armature should be as small as possible but at the same time very robust. The drive mechanism can be configured as a pneumatic, electrical, or an angled electrical drive, with a pneumatic drive representing the preferred solution. The holder armature can also be manually actuated.

BRIEF DESCRIPTION OF THE DRAWINGS

Several different examples of embodiments of a holder armature for interchangeable measuring probes are described hereinafter with references to the drawing figures, wherein identical parts are identified by identical reference numbers and wherein.

DETAILED DESCRIPTION OF A PREFERRED EMBODIMENT

Figure 1:
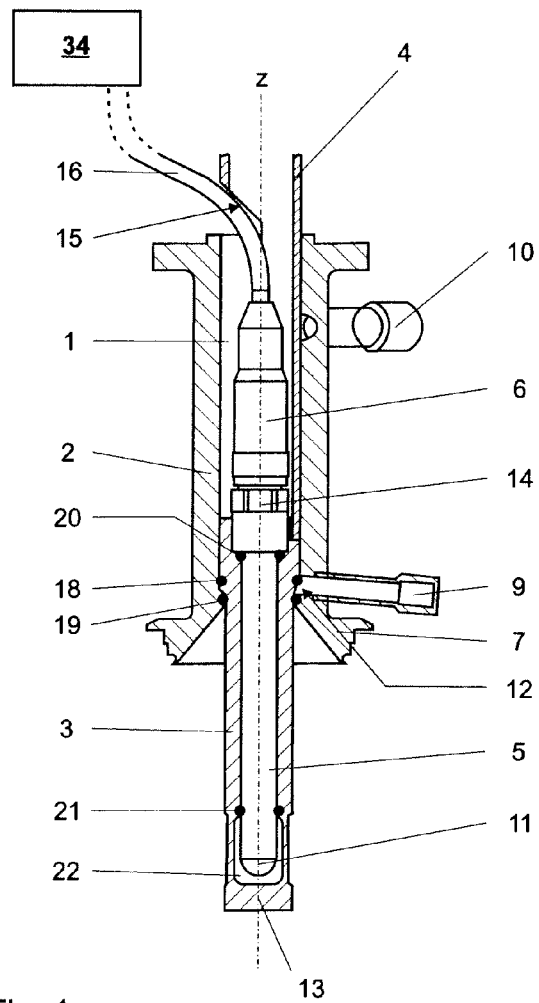
FIG. 1 is a partial side sectional view of a holder armature with a treatment chamber and with a measuring probe, in the measuring position.
Figure 2:
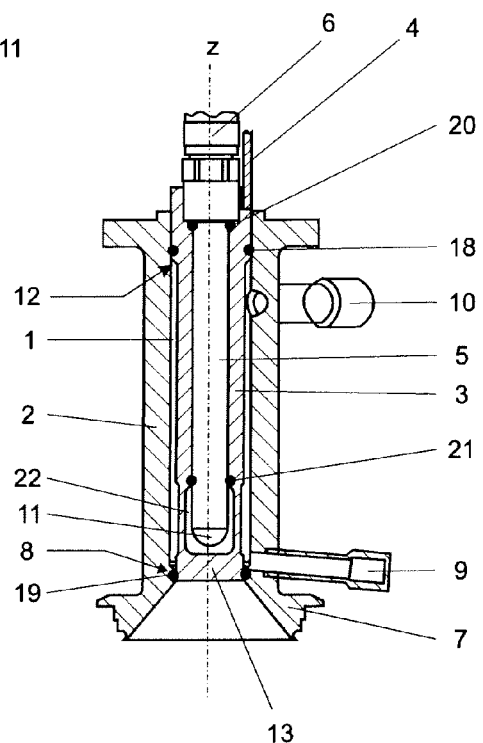
FIG. 2 is a partial side sectional view of the FIG. 1 device, shown in the rest position.

A partial representation of a probe-holder armature with a treatment chamber and a measuring probe is shown in FIG. 1 in the measuring position and in FIG. 2 in the rest position. The following description relates to a very large extent to both figures.

The holder armature has a housing 2 which includes a treatment chamber 1, with an immersion tube 3 that is axially movable in the housing 2, with a drive element 4 that is releasably connected to the immersion tube 3, and with a measuring probe arranged in the immersion tube 3. The measuring probe has a sensor 5 and a sensor head 6. The top part of the holder armature (in relation to the drawing), which is not shown in FIG. 1 and which includes the drive mechanism among other elements, is shown in more detail in FIGS. 3 to 5.

The housing 2 has, at the end that is nearer to the measurement medium, a flange 7 which allows the holder armature to be connected to any desired receptacle such as for example a pipe conduit or a reaction vessel. The design of the flange 7 is dependent, among other factors, on the field of application. The flange 7 can be a standardized process flange or a process connection as well as a special flange that may have been made to order at a customer's request.

Such flanges or connectors for the most diverse kinds of reaction vessels and process systems are generally known and will therefore not be discussed in detail herein.

Inside the housing 2 a continuous chamber, which in this example is designed as a treatment chamber 1, extends along the axis drawn in a broken line. In the most basic case, the treatment chamber 1 is at least partially open towards the ambient environment, when the measuring probe is deployed into the measurement medium and the holder armature is in the measuring position.

The treatment chamber 1 serves the purpose to treat the sensor 5, above all a sensitive element 11 at the end of the sensor 5 that faces towards the measurement medium, with different kinds of treatment agents. These treatment agents can include various liquids or gases; in addition, it is possible to evacuate the chamber 1, so that the sensor and primarily the sensitive element 11 can be cleaned in the treatment chamber 1 and/or the measuring probe can be calibrated and/or its ability to function properly can be tested. Together with the sensor 5, a large part of the exterior surface of the immersion tube 3 can be cleaned in the treatment chamber 1. The treatment agents can in this example be directed into the treatment chamber 1 and subsequently removed from the latter by way of two conduit terminals 9, 10 on the housing 2. For the best treatment result possible, the conduit terminals 9, 10 are arranged at opposite ends of the treatment chamber.

The immersion tube 3 has in its interior a hollow space whose diameter and shape is matched to the outside diameter and shape of the sensor 5, so that the immersion tube 3 can accommodate at least the sensor 5. At the end facing towards the measurement medium, the immersion tube 3 is perforated so that an area 22 is formed which is at least partially open towards the measurement medium. The closure of the immersion tube 3 towards the measurement medium is formed by a massive plug 13. In the measurement position, the sensor 5 is arranged in the immersion tube in such a way that the sensitive element 11 is located in the open area 22 where it can enter directly into contact with the measurement medium.

The end of the immersion tube 3 that is farther from the measurement medium is open and has a connector that serves to secure a measuring probe, so that at least the sensor 5 can be inserted in the immersion tube 3 and the measuring probe can be fastened to the immersion tube 3. This connector is covered from view in this illustration by a connector bushing 14, for example a cap nut which is arranged at the measuring probe between the sensor 5 and the sensor head 6. The known state of the art offers a variety of connectors for the fastening of measuring probes. The latter will therefore not be discussed in detail herein.

The end of the immersion tube 3 that is farther from the measurement medium further includes a closure element (see FIGS. 3 to 5) which provides a releasable connection of the immersion tube 3 with the drive element 4. The immersion tube 3 and the drive element 4 can for example be connected by means of a bayonet connection, a screw connection, a plug-in connection, or other connector elements of the known state of the art.

The drive element 4 is preferably configured as a sleeve of a design that is partially open in the area towards the measurement medium, for example in the form of a half shell or a sleeve segment (see also FIGS. 3 and 4), so that the drive element 4 can accommodate the sensor head 6. The transition from the closed to the open sleeve is preferably cut at an oblique angle, so that the drive element 4 simultaneously serves as cable guide for a cable 16 that is fastened to the sensor head 6. The cable 16 is connected to a processing-and/or control unit or to a process control center 34, and it can be additionally secured on the outside of the drive mechanism housing which is not shown in this drawing.

To seal the different parts of the holder armature against the measurement medium or against the ambient environment, the holder armature has several seals. At least a first seal 18 is arranged at the upper end (relative to the drawing FIG. 1) of the immersion tube 3 on the outside of the latter. A second seal 19 is arranged in the narrowed-down area of the housing 2 on a ledge 8. These two seals 18, 19 serve to seal off the treatment chamber against the measurement medium and against the ambient environment in the measuring position as well as in the rest position.

Further seals are located inside the immersion tube 3 between the immersion tube 3 and the sensor 5. A third seal 20 is located at the far end of the immersion tube 3 from the measurement medium, in relation to FIG. 1 slightly above the seal 18, and a fourth seal 21 is located above the area 22 that is open towards the measurement medium. The third and fourth seals 20, 21 seal off the interior of the immersion tube 3 as well as the sensor head 6 against invading media and also serve to hold the sensor 5 in place in the immersion tube 3.

The seals 18 to 21 are preferably O-rings of a chemical-resistant, sterilizable material.

In the measurement position shown in FIG. 1, a large part of the immersion tube 3 as well as the sensitive element 11 are in contact with the measurement medium. The immersion tube 3 is advanced into a measurement medium, or in other words, the measuring probe is deployed. The sensor head 6 as well as the part of the drive element 4 surrounding the sensor head 6 are located inside the treatment chamber 1.

The conduit terminals 9, 10 for the treatment chamber 1 are arranged at or in the housing 2 in such a way that in the measurement position, their openings which are directed towards the treatment chamber 1 are sealed and closed off by the immersion tube 3 or by the drive element 4, so that besides a shut-off valve which may be arranged for example in the supply conduits, there exists a mechanical barrier as a protection against an entry of treatment agents which may occur by mistake. The treatment chamber 1 in the measurement position is open towards the ambient environment and the seals 18, 19 tightly close off the holder armature against invading media.

In the rest position shown in FIG. 2, the immersion tube 3 and the sensor 5 that is arranged inside the immersion tube are positioned in the treatment chamber 1. The part of the immersion tube 3 that lies between the seal 18 and the plug 13 has a smaller diameter than the interior of the treatment chamber 1, so that almost all parts of the holder armature that are in contact with the measurement medium during a measurement can be treated in the treatment chamber 1. The openings of the connector terminals 9, 10 leading to the treatment chamber 1 are no longer blocked. Treatment agents such as liquids and/or gases which have been delivered inside for a calibration and/or cleaning can circulate and rinse the immersion tube 3 as well as the sensitive element 111 arranged in the open area 22. Only the bottom of the plug 13 is still in contact with the measurement medium and can be treated with methods that are also used to clean the vessel containing the measurement medium.

A change from the measurement position (see FIG. 1) into the rest position (see FIG. 2) necessitates that the drive element 4, the immersion tube 3 as well as the measuring probe that is arranged in the immersion tube 3 be moved in the direction towards the drive mechanism housing, i.e. upwards in relation to FIGS. 1 and 2. This has the consequence that in the rest position, the sensor head 6 as well as at least in part the drive element 4 are located in the housing attachment.

In the rest position (see FIG. 2), the second seal 19 which is arranged in the housing 2 on the constriction formed by the ledge 8 seals the treatment chamber 1 against the measurement medium, so that treatment agent cannot leak from the treatment chamber 1 into the measurement medium and vice versa. The seal 18 is now located between the respective ends of the immersion tube 3 and of the treatment chamber 1 that are farther from the medium and seals off the treatment chamber 1 from the ambient space.

The preferred embodiment shown in FIGS. 1 and 2 has a further safety feature in the form of a ledge 8 which is arranged inside the housing 2 in the area closest to the measurement medium. The ledge 8 constricts the housing 2 at this location and thus simultaneously represents one end of the treatment chamber 1. The ledge 8 serves as a limit stop for the immersion tube 3 and, in relation to the drawing, is located above the flange 7.

The immersion tube 3 is arranged to be axially movable in the housing 2. The immersion tube 3 is formed in such a way that it can seal the treatment chamber 1 against the measurement medium as well as against the ambient space (see FIG. 2). The part of the immersion tube 3 which in the measuring position is in contact with the measurement medium therefore has a smaller outside diameter than the part which in the measuring position remains inside the housing 2, so that the part of the immersion tube 3 that points towards the measurement medium can slide through the narrowed-down portion of the housing 2.

The sections with different outside diameters of the immersion tube have a transition area in the form of a step 12 which in the measuring position is seated against the ledge 8 of the treatment chamber 1 and thus defines a fixed position for the immersion tube 3 in the housing 2 when the immersion tube 3 is in the measuring position.

Figure 3:
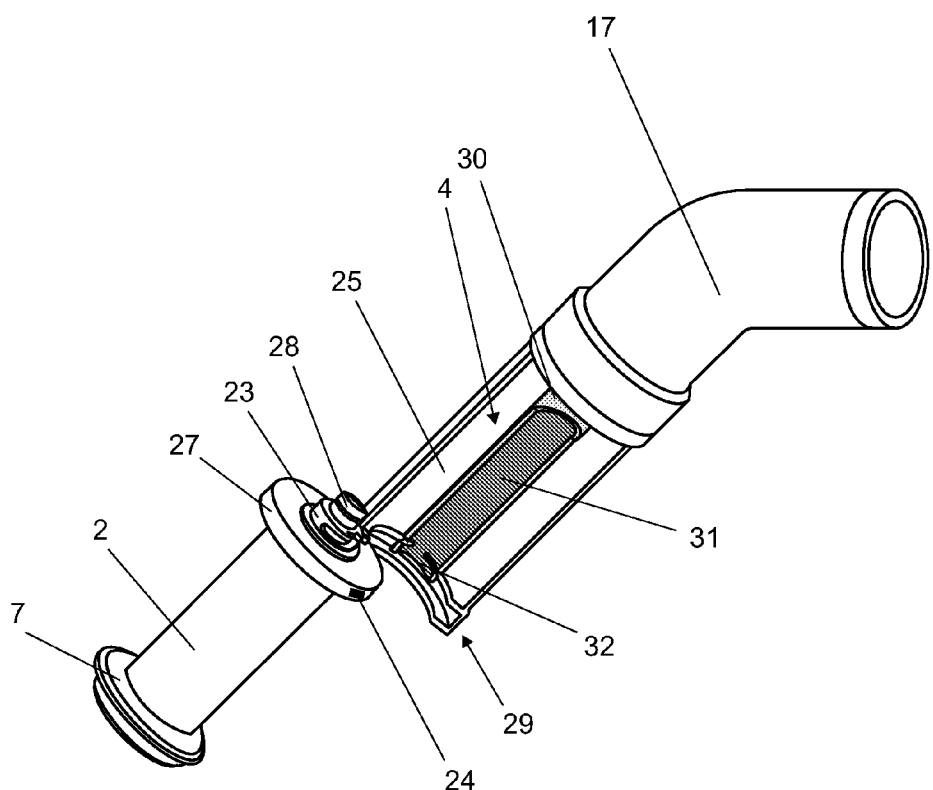
FIG. 3 is a perspective view of a holder armature without treatment chamber and with an angled drive mechanism in an uncoupled condition.
Figure 4:
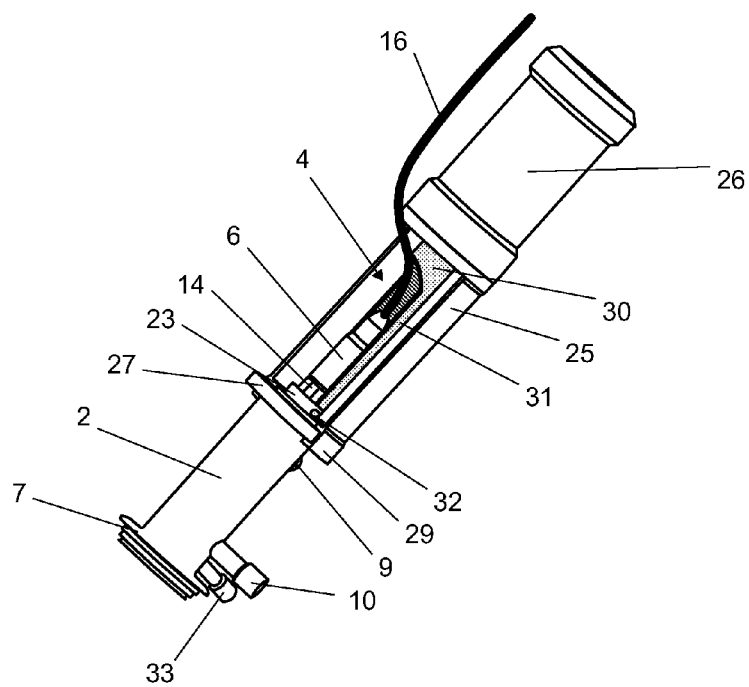
FIG. 4 is a perspective view of the holder armature with a treatment chamber and with a measuring probe in the rest position.

In the rest position, the measuring probe can either be treated with treatment agents that are circulated through the treatment chamber, or it can be removed from the holder armature after the connector bushing 14 has been released and the drive element 4 has been uncoupled and moved relative to the housing 2, with the conduits into the treatment chamber 1 blocked and the treatment chamber in an empty state (see FIGS. 3 and 4). To ensure that a treatment in the treatment chamber 1 can only be performed when a measuring probe is in place, the holder armature has at least one safety element such as for example a contact pin (not visible in the drawing) arranged inside the part of the immersion tube that points away from the measurement medium, wherein the contact pin is actuated by a measuring probe that is set in place and sends a signal to the processing- and/or control unit which will then open the inlet to the treatment chamber 1.

A further example of an embodiment of a holder armature for a measuring probe is shown in perspective in FIG. 3. The holder armature has a housing 2 with a safety element 24 arranged on it and with an immersion tube arranged in the housing 2, of which the drawing only shows the connector element 23 for the connection to the drive element 4 and the connection 28 for a measuring probe which is not shown here. The holder armature further includes a housing attachment 25 releasably connected to the housing 2 and an angled drive mechanism housing 17 for a drive mechanism designed to be set at an angle. In the interest of more clarity, the housing attachment 25 is shown at least partially open.

The housing 2, as well as the holder armature, is of a substantially cylindrical shape, but other configurations could also be realized. The housing 2 has a flange 7 at the end that faces the measurement medium. At the opposite end from the measurement medium, the housing 2 terminates in a flat, disk-shaped part 27 which stands out from the cylinder.

Inside the housing 2, the immersion tube is arranged so that it can slide in the housing. The housing 2 in this embodiment is not designed as a treatment chamber and also has no conduit terminals for treatment agents. The housing 2 serves primarily as a guide and holder for the immersion tube which is arranged so that it can slide axially inside the housing. The dimensions, design and function of the interior of the housing 2 in regard to the arrangement of the immersion tube are analogous to those of the treatment chamber shown in FIGS. 1 and 2.

The immersion tube is arranged in the housing 2 and can accommodate a measuring probe, and in particular the sensor of a measuring probe. To secure the measuring probe, the immersion tube is equipped with a connector 28 which in the rest position protrudes from the housing 2 at the far end from the measurement medium. The connector 28 can have the form of any of the known measuring probe connectors that can be coupled to the connector bushing of the measuring probe which was mentioned in the description of FIGS. 1 and 2. The housing 2 is connected releasably with a housing attachment 25 which is preferably designed so that it can swivel about an axis that is arranged off-center and close to the outside border, along which axis there is a means for connecting the housing 2 with the housing attachment 25. Said means can be configured for example as a pin, peg or rod. The housing attachment 25 and the housing 2 can be separated completely from each other. The housing attachment 25 serves to protect the drive element 4 which is connected to the drive mechanism in the drive mechanism housing 17 from outside influence factors, and to provide the connection between the housing 2 and the drive mechanism housing 17. Preferably, but not as an absolute requirement, the housing attachment 25 is solidly connected to the drive mechanism housing 17 and can be moved only together with the latter.

The housing attachment 25 has a groove 29 at the end that is nearer to the measurement medium, which groove can fit precisely over the outside edge of the disk-shaped part 27.

The holder armature in FIG. 3 is shown without the measuring probe and with an at least partially opened housing attachment 25. Arranged at the outside edge of the disk-shaped part 27 is an electronic and/or mechanical safety element 24 which prevents the immersion tube 3 or a measuring probe arranged in the latter from being deployed into a measurement medium when the housing attachment 25 is swiveled out in relation to the housing 2 or in an open state. When the housing attachment 25 is closed, it comes into contact with the safety element 24 and thereby releases a lock, so that the immersion tube 3 can be advanced into a measurement medium. The safety element 24 can be configured for example as a key or other element that is responsive to being depressed and which cooperates with a bolt that engages a recess in the immersion tube 3. When the housing attachment 25 pushes the safety element 24 into the housing 2, the bolt is released from a recess in the immersion tube 3, and the latter can be moved by means of the drive mechanism. When the housing attachment 25 is released from the housing 2, the bolt is reengaged in the recess. In addition to establishing a mechanical lock, the safety element 24 as well as further safety elements can also be, e.g., electrically connected to the drive mechanism and/or to a process control center or a processing- and/or control unit to control—in the simplest case—the operating state (on/off) of the drive mechanism.

The drive element 4 is substantially an elongated sleeve that is connected to the drive mechanism which is arranged in the drive mechanism housing 17. The part of the drive element 4 that is farther from the measurement medium has the form of a closed ring sleeve 30, while the part that is nearer to the measurement medium is an at least partially open sleeve segment 31 ending towards the measurement medium in a connector element 32 which can cooperate with the connector element 23 of the immersion tube. In the rest position, the end of the closed ring sleeve 30 is located in the drive mechanism 26.

When the housing attachment is closed, the connector elements 23 and 32 are engaged with each other so that a releasable connection is established between the immersion tube and the drive element 4. The connector elements 23, 32 are designed so that they engage and mesh with each other when the housing attachment 25 is closed and are easily disengaged again from each other when the housing attachment 25 is opened. A further safety element is triggered upon the correct engagement of the connector elements 23, 32, so that the immersion tube can only be advanced into a measurement medium if the drive mechanism is correctly connected to the immersion tube by way of the drive element. A deployment of the immersion tube is prevented even though the drive element is in contact with the immersion tube, if the connector elements 23, 32 are not engaged.

The safety element described in the context of FIGS. 1 and 2 prevents the deployment of the immersion tube 3 if there is no measuring probe inside it. The safety element 24 prevents a deployment of the immersion tube 3 when the housing attachment 25 is open. A further safety element prevents a deployment of the immersion tube when the connector means 32, 23 are released. In a holder armature equipped with all three safety elements, a deployment of the immersion tube 3 into a measurement medium is possible only if a measuring probe is in the armature, the housing attachment 25 is closed, and the drive mechanism is connected to the immersion tube through the drive element (see also FIGS. 4 and 5).

A further example of an embodiment of a holder armature in the rest position with a measuring probe set in place, with the housing attachment 25 closed, and with a drive mechanism housing 26 for a straight-line drive mechanism is shown in FIG. 4 in a perspective view. The housing attachment 25 is shown again at least partially open towards the ambient environment.

The measuring probe is connected by means of the connector bushing 14 to the immersion tube which is in its rest position inside the housing 2 and is not visible in this representation. The drive element 4, by means of the connector elements 23, 32, is likewise connected to the immersion tube, and the groove 29 of the housing attachment 25 embraces the outside edge of the disk-shaped part 27. In the rest position illustrated here, the sensor head 6 is inside the sleeve segment 31 which is located in the housing attachment 25. The cable 16 which is attached to the sensor head 6 is routed to the outside of the holder armature through the drive element 4, in particular at the transition 15 between the sleeve 30 and the sleeve segment 31. The housing attachment 25 has a passage opening designed for this purpose.

In this embodiment, the housing 2 has three conduit terminals 9, 10, 33 as inlets and outlets for treatment agents to and from the treatment chamber which is arranged in the housing 2.

Figure 5:
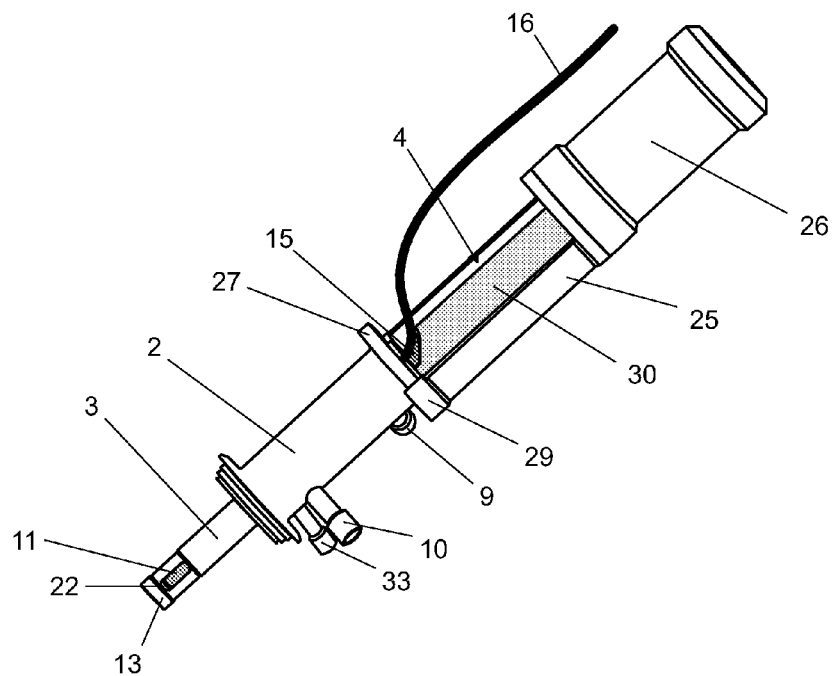
FIG. 5 is a perspective view of the FIG. 4 device in the measuring position.

FIG. 5 shows the same embodiment of a probe-holder armature as FIG. 4, but in the measuring position. The immersion tube 3 has been moved by the drive element 4 and now protrudes from the housing 2 for example into a measurement medium and can enter into contact with the latter. In the area of the housing attachment 25, this representation brings primarily the closed sleeve 30 of the drive element 4 into view. The sleeve segment 31 is located almost completely in the interior of the housing 2, so that only a small opening remains in the area of the housing attachment, through which the cable 16 passes to the outside, if a measuring probe with a cable is used.

In the deployment into a measurement medium, the immersion tube 3, the drive element 4 and the measuring probe arranged inside it are advanced axially towards the measurement medium by means of the drive mechanism which is arranged in the drive mechanism housing 26.

The measuring probe can be installed or uninstalled only in the rest position with the housing attachment 25 in the open state, because in the measuring position the access to the immersion tube and thus to the measuring probe is blocked by the closed part 30 of the drive element 4. When the measuring probe is being treated in the treatment chamber, a removal of the measuring probe is prevented primarily by the substantially closed housing attachment 25.

For better clarity, the housing attachment 25 in all of the FIGS. 3 to 5 is shown partially open to the ambient environment. During operation it is advantageous if the housing attachment is substantially closed so that neither liquids nor dust particles can enter through the housing attachment into the probe-holder armature. A closed housing attachment can be realized by closing off the opening that is required for the exchange of a measuring probe, for example by means of a separate cap, a movable closure element or a flexible bellows, wherein the closure element can have a passage for a cable.

The probe-holder armature according to the invention can be realized with as well as without a treatment chamber, with preference being given to the version that includes a treatment chamber.

The immersion depth of the measuring probe can be changed by the displacement height of the holder armature, i.e. the travel distance of the immersion tube in the housing. However the maximum immersion depth is determined by the length of the measuring probe being used and in particular by the length of the sensor being used.

Dependent on the length of the measuring probe being used, at least the length of the immersion tube should be made to match. Further adaptations to different probe lengths can occur by changing the length of the housing and/or the housing attachment. If the probe-holder armature has a treatment chamber, it is preferred to adapt the housing attachment because the outside of the immersion tube can be cleaned already when the immersion tube is pulled through the treatment chamber and because during a treatment the sensitive element most of all has to be located inside the treatment chamber. It would further be conceivable that if particularly long sensors are being used, to arrange a major part of the holder armature in the interior of the vessel that contains the measurement medium. Thus, depending on the design of the probe-holder armature, the latter can be used with all of the conventional commercially available sensor lengths.

The design of the immersion tube 3 and the arrangement of the open area 22 at the end of the immersion tube that is nearer to the medium represents a preferred embodiment of the immersion tube which is favored above all for measuring probes and sensors in which the sensitive element is located at the end. The immersion tube can also have one or more windows in other places, so that measuring probes with sensors whose sensitive elements are not arranged at the end can likewise be installed in the holder armature and used for the measurement of different parameters of the measurement medium.

The housing 2 can have a ledge 8 as shown in FIGS. 1 and 2, to serve as a displacement limiting stop. The purpose of this stop is to prevent the immersion tube from entering too far into the vessel to which the probe-holder armature is connected. The housing 2 can also be designed without this ledge 8, in which case the seal 19 can be arranged in a groove on the inside of the housing, and the immersion tube 3 can be designed with a uniform inside diameter.

The drive element in the illustrated embodiments has been shown as a partially open sleeve. Other design possibilities include individual rods, as well as sleeve segments with openings of different sizes, or also a completely closed sleeve if a measuring probe without cable is used.

The drive element and the housing attachment have the effect that the drive mechanism and the housing are uncoupled from each other in regard to the conduction of heat, so that heat generated in the drive mechanism has no influence on a measuring probe that is arranged in the immersion tube in the housing.

What is claimed is:

1. An armature for an interchangeable measuring probe having a sensor with a sensitive element at a first end of the measuring probe and a sensor head at a second end thereof, comprising:
   a housing;
   a drive mechanism housing;
   a drive mechanism arranged in the drive mechanism housing;
   a housing attachment, arranged between the housing and the drive mechanism housing, the housing attachment being releasably connected to the housing;
   an immersion tube, adapted for removably receiving therein at least the sensor and the sensitive element, the immersion tube being axially movable in the housing between a rest position and a measuring position, with the entire immersion tube remaining outside of the housing attachment and the sensor head remaining outside of the drive mechanism housing, during the axial movement when the measuring probe is received in the immersion tube; and a drive element that releasably couples the immersion tube to the drive mechanism.

2. The armature of claim 1, wherein:
the housing attachment is adapted to allow any conduits extending from the probe to pass therethrough.

3. The armature of claim 2, wherein:
the drive element is in the housing attachment.

4. The armature of claim 3, wherein:
the housing further comprises a treatment chamber for the measuring probe.

5. The armature of claim 4, further comprising:
at least one seal that performs at least one of the functions of sealing the treatment chamber against a measurement medium while in the measuring position and sealing the treatment chamber against the measurement medium and the ambient environment while in the rest position,
the at least one seal located on at least one of the immersion tube and the housing.

6. The armature of claim 4, wherein:
the treatment chamber comprises a conduit terminal, through which a treatment agent is supplied to or removed from the treatment chamber.

7. The armature of claim 6, further comprising:
at least one safety element, for preventing axial movement of the immersion tube under at least one of the following conditions: (a) when no measuring probe is in the immersion tube; (b) when the immersion tube is not connected to the drive element; and
(c) when the housing attachment is released from the housing.

8. The armature of claim 5, wherein:
the at least one safety element comprises an electronic sensor that sends a signal to at least one device connected to at least one of the armature and the probe, the device selected from the group consisting of: a processing unit, a control unit and a control center.

9. The armature of claim 8, for use when the measuring probe further comprises a sensor and a sensor head, wherein:
the drive element and immersion tubes are structured such that placement of the probe in the armature locates the sensor in the immersion tube and the sensor head in the drive element.

10. The armature of claim 9, wherein:
the measuring probe is removable from the armature only in the rest position, with the housing attachment is released from the housing and with the drive element disconnected from the immersion tube.

11. The armature of claim 10, further comprising:
at least one seal that performs at least one of the functions of sealing the treatment chamber against a measurement medium while in the measuring position and sealing the treatment chamber against the measurement medium and the ambient environment while in the rest position,
the at least one seal located on at least one of the immersion tube and the housing.

12. The armature of claim 11, wherein:
the drive mechanism is a linear drive mechanism.

13. The armature of claim 11, wherein:
the drive mechanism is driven pneumatically or electrically.

14. The armature of claim 7, wherein:
the at least one safety element comprises a locking element that is actuated either mechanically or electronically.

15. The armature of claim 6, further comprising:
at least one safety element, for controlling the inflow of the treatment agent into the treatment chamber.

16. The armature of claim 15, wherein:
the at least one safety element comprises a locking element that is actuated either mechanically or electronically.

17. The armature of claim 15, wherein:
the at least one safety element comprises an electronic sensor that sends a signal to at least one device connected to at least one of the armature and the probe, the device selected from the group consisting of: a processing unit, a control unit and a control center.

18. The armature of claim 1, further comprising:
at least one safety element, for preventing axial movement of the immersion tube under at least one of the following conditions: (a) when no measuring probe is in the immersion tube; (b) when the immersion tube is not connected to the drive element; and (c) when the housing attachment is released from the housing.

19. The armature of claim 1, for use when the measuring probe further comprises a sensor and a sensor head, wherein:
the drive element and immersion tube are structured such that placement of the probe in the armature locates the sensor in the immersion tube and the sensor head in the drive element.

20. The armature of claim 1, wherein:
the measuring probe is removable from the armature only in the rest position, with the housing attachment released from the housing and with the drive element disconnected from the immersion tube.

21. The armature of claim 1, wherein:
the drive mechanism is a linear drive mechanism.

22. The armature of claim 1, wherein:
the drive mechanism is driven pneumatically or electrically.

23. The armature of claim 1, wherein:
the drive element is in the housing attachment.

* * * * *

UNITED STATES PATENT AND TRADEMARK OFFICE
CERTIFICATE OF CORRECTION

PATENT NO. : 7,594,449 B2  
APPLICATION NO. : 11/463319  
DATED : September 29, 2009  
INVENTOR(S) : Tottewitz et al.

Page 1 of 1

It is certified that error appears in the above-identified patent and that said Letters Patent is hereby corrected as shown below:

In column 8, line 17, please delete "sensitive element 111" and insert -- sensitive element 11 --.

In column 13, line 31, please delete "claim 5," and insert -- claim 7, --.

In column 13, line 45, please delete "is".

Signed and Sealed this

Twenty-seventh Day of October, 2009

David J. Kappos  
*Director of the United States Patent and Trademark Office*

UNITED STATES PATENT AND TRADEMARK OFFICE
CERTIFICATE OF CORRECTION

PATENT NO. : 7,594,449 B2
APPLICATION NO. : 11/463319
DATED : September 29, 2009
INVENTOR(S) : Tottewitz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 530 days.

Signed and Sealed this

Twenty-eighth Day of September, 2010

David J. Kappos
*Director of the United States Patent and Trademark Office*